US008759607B2

(12) United States Patent
Harada et al.

(10) Patent No.: US 8,759,607 B2
(45) Date of Patent: Jun. 24, 2014

(54) GENOTYPES, ALLELES AND MOLECULAR MARKERS ASSOCIATED WITH ASIAN SOYBEAN RUST, AS WELL AS METHODS, PROCESSES AND USES THEREOF

(75) Inventors: Arlindo Harada, Cambé (BR); Éberson Sanches Calvo, Cambé (BR); Romeu Afonso de Souza Kiihl, Cambé (BR); Alexandre Garcia, Cambé (BR)

(73) Assignee: TMG—Tropical Melhoramento e Genetica Ltda. (BR)

( * ) Notice: Subject to any disclaimer, the term of this patent is extended or adjusted under 35 U.S.C. 154(b) by 772 days.

(21) Appl. No.: 12/809,855

(22) PCT Filed: Dec. 16, 2008

(86) PCT No.: PCT/BR2008/000392
§ 371 (c)(1),
(2), (4) Date: Sep. 21, 2010

(87) PCT Pub. No.: WO2009/079729
PCT Pub. Date: Jul. 2, 2009

(65) Prior Publication Data
US 2011/0191893 A1 Aug. 4, 2011

(30) Foreign Application Priority Data
Dec. 21, 2007 (BR) .................................... 0704999

(51) Int. Cl.
*A01H 1/04* (2006.01)
*A01H 1/02* (2006.01)
*A01H 5/10* (2006.01)

(52) U.S. Cl.
USPC ........... 800/267; 800/265; 800/266; 800/312; 435/6.11

(58) Field of Classification Search
None
See application file for complete search history.

(56) References Cited

FOREIGN PATENT DOCUMENTS
WO  WO 2008/054546 A2  5/2008

OTHER PUBLICATIONS

Burnham et al. (Crop Science; (2003); vol. 43 No. 1; pp. 101-105).*
Hnetkovsky et al. (Crop Science; (1996); vol. 36; pp. 393-400); only abstract attahced,1 page.*
Alzate-Marin, et al., "Seleção Assistida por Marcadores Moleculares Visando ao Desenvolvimento de Plantas Resistentes a Doenças, com Ênfase em Feijoeiro e Soja," *Fitopatol. bras.*, 2005, vol. 30(4), 333-342.
Collard, et al., "An introduction to markers, quantitative trait loci (QTL) mapping and marker-assisted selection for crop improvement: The basic concepts," *Euphytica*, 2005, vol. 142, pp. 162-196.
Frederick, et al., "Polymerase Chain Reaction Assays for the Detection and Discrimination of the Soybean Rust Pathogens *Phakopsora pachyrhizi* and *P. meibomiae*," *Phytopathology*, 2002, vol. 92(2), pp. 217-227.
Garcia, et al., "Molecular mapping of soybean rust (*Phakopsora pachyrhizi*) resistance genes: discovery of a novel locus and alleles," *Theor Appl Genet*, 2008, vol. 117, pp. 545-553.
Hyten, et al., "Map Location of the *Rpp1* Locus That Confers Resistance to Soybean Rust in Soybean," *Crop Science*, 2007, vol. 47, pp. 837-840.
Meesang et al., "Soybean cultivar identification and genetic purity analysis using microsatellite DNA markers," *Seed Sci. & Technol.*, 2001, vol. 29, pp. 637-645.
Monteros, et al., "Mapping and Confirmation of the 'Hyuuga' Red Brown Lesion Resistance Gene for Asian Soybean Rust," *Crop Science*, 2007, vol. 47, pp. 829-836.
Young, N.D., "QTL Mapping and Quantitative Disease Resistance in Plants," *Annu. Rev. Phytopathol.*, 1996, vol. 34, pp. 479-501.

* cited by examiner

*Primary Examiner* — David T Fox
*Assistant Examiner* — Jared Shapiro
(74) *Attorney, Agent, or Firm* — Sheridan Ross P.C.

(57) ABSTRACT

The present invention relates to screening methods for rust resistance or tolerance, in particular, Asian soybean rust (ASR—*Phakopsora pachyrhizi*). In addition, the present invention relates to the use of molecular markers for the *Glycine* genus, in particular, for the *Glycine max* species. The present invention further relates to a method for identifying loci with quantitative and/or qualitative traits associated with rust resistance or tolerance in plants by means of molecular markers. Said markers can be used for assisted screening in improvement programs directed to selecting disease-resistant or -tolerant plants. The present invention also relates to gene pyramiding related to rust resistance. The markers of the present invention are also useful for the positional cloning of rust-resistant or -tolerant genes. Also disclosed are a method for obtaining disease-resistant or -tolerant cultivars, process for obtaining a plant population and a method for controlling diseases in a plant population. Another object of the present invention is the use of species from the *Glycine* genus as a source of resistance for obtaining ASR-resistant or tolerant cultivars.

5 Claims, 5 Drawing Sheets

| Fungicide application stage | | | | | | | TESTEMUNHA |
|---|---|---|---|---|---|---|---|
| R2 | R3 | R4 | R5.1 | R5.3 | R5.4 | R2; R4; R5.5 | |
| 08/02 | 14/02 | 23/02 | 01/03 | 07/03 | 15/03 | 08/02; 23/02 e 15/03 | |

BRS 133: good control, 6 days short window; late; AACPD - 476.2; AACPD - 781.2

Line: good control, 21 days long application window; late; AACPD - 142.5; AACPD - 291.3

FIG 7

GENOTYPES, ALLELES AND MOLECULAR MARKERS ASSOCIATED WITH ASIAN SOYBEAN RUST, AS WELL AS METHODS, PROCESSES AND USES THEREOF

FIELD OF THE INVENTION

The present invention relates to screening methods for rust resistance or tolerance, in particular, Asian soybean rust (ASR—*Phakopsora pachyrhizi*).

In addition, the present invention relates to the use of molecular markers for the *Glycine* genus, in particular, for the *Glycine max* species. The present invention further relates to a method for identifying loci with quantitative and/or qualitative traits associated with rust resistance or tolerance in plants by means of molecular markers.

Said markers can be used for assisted screening in improvement programs directed to selecting disease-resistant or -tolerant plants. The present invention also relates to gene pyramiding related to rust resistance.

In addition, the markers of the present invention are useful for the positional cloning of rust-resistant or -tolerant genes.

Also disclosed are a method for obtaining disease-resistant or -tolerant cultivars, a process for obtaining a plant population and a method for controlling diseases in a plant population.

A further object of the present invention is to use species of the *Glycine* genus, that is, PI 459025, PI 230970, PI 200456, PI 224270, PI 200526, PI 200487, PI 471904, as a source of resistance for obtaining ASR-resistant or -tolerant cultivars.

BACKGROUND OF THE INVENTION

Soybean (genus *Glycine*) belongs to the Fabaceae family (leguminosae), as well as bean (*Phaseolus*), lentil and pea (*Pissum*), and is a protein-rich grain, grown as food, both for human and animals. The word soy comes from Japanese shoyu and originated in China. The Fabaceae family is one of the largest plant families, also known as Leguminosae, having a broad geographic distribution. There are approximately 18,000 species in more than 650 genera. The typical fruit of this type of family is the legume, also known as pod (there are exceptions). It is subdivided into 3 very different subfamilies: Faboideae (or Papilionoideae), Caesalpinioideae (or Caesalpiniaceae) and Mimosoideae (or Mimosaceae). The variation in name is due to the current coexistance of more than one classification system. The literature describes that the roots of almost all species in this family live in symbiosis with bacteria of the *Rhizobium* genus and the like, responsible for nitrogen fixation in the air, a relevant and significant ecological characteristic. Furthermore, they are of high economic value for food production.

Soybean is considered an important crop and is highly valued by world agriculture. In this sense, one of the major objectives of the soybean breeders is to develop more stable, productive and disease-resistant varieties, such as, rust-resistant varieties, for instance. One of the main reasons for this concern is to maximize grain yield for human and animal consumption. In order to attain said objects, the breeder should select and develop cultivars having superior traits over those available in the market.

Borém (1998) defines improvement as "the art and science that aim at the genetic modification of plants to render them more useful to men". Breeder Manoel Abílio de Queiroz (2001) (Queiroz, M. A., 2001 "Melhoramento Genético no Brasil—realizaçõoes e perspectivas". In: Recurso Genéticos e Melhoramento de Plantas, cap. 1. pg. 1-28.) comments on this respect on a broader perspective, contemplating the entire development of agriculture in the last ten thousand years, and its role in changing the habits of human populations that abandoned nomadism and adopted sedentarism. This happened when people decided to abandon extractivism to start growing crops that were more suitable for their survival. This practice has lasted for a long period and caused changes in the gene frequencies of the chosen species, bringing significant benefits to the world agriculture. It is known that the domestication of new species is relatively recent and very limited, and that most species that feed humanity were domesticated in remote times, particularly grains.

The same author reports that with the advent of genetic improvement after the discovery of Mendel's Laws, science started to play a leading role in the development of significant crops for human consumption. In this respect, texts were published in the most different areas of knowledge and in different branches of genetics, including DNA genetic markers, which are relevant for monitoring genetic plant improvement with a view to making it more efficient in the search for enhancing traits that may meet society's needs.

The enhancement of plants aims at obtaining plant varieties that are superior to those available in the market, either in the production of grains, green mass or fibers, in resistance to pests and diseases, or in higher protein and oil content, fiber quality or other traits of interest (Conagin, A.; Ambrosano, G. M. B.; Nagai, V. Poder discriminativo da posição de classificação dos testes estatísticos na seleção de genótipos. Bragantia, v. 56, no. 2, p. 403-417, 1997.).

Among the main contributions of the soybean improvement in Brazil is the development of varieties capable of adapting to lower latitudes and resistant to major diseases (Arias, C. A. A. et al. Melhoramento e Biotecnologia: ferrugem da soja. In: IV Brazilian Soybean Congress held on Jun. 5-8, 2006. Londrina (Proceedings)). The same authors also report that studies involving genetic resistance provided positive results in helping to solve disease problems. Some of the diseases include: frogeye leaf spot (*Cercospora sojina*), soybean stem canker (*Diaporthe phaseolorum* f.sp. *meidionallis*), powdery mildew (*Microsphaera diffusa*) and soybean cyst nematode (*Heterodera glycines*). In addition, Brogin (2005), (Brogin, R. L. Mapeamento de genes de resistência à ferrugem e de QTL's envolvidos na resistência à Septoriose. 2005. Dissertation (Doctorate in Genetics and Plant Improvement—Escola Superior de Agricultura "Luiz de Queiroz", E-SALQ/USP, Piracicaba, SP.) described studies on resistance to bacterial pustule, bacterial blight, brown stem rot, stem necrosis virus and soybean mosaic virus.

In the case of soybean, it is known that the improvement has been made by the introduction of materials, selection and hybridization (artificial crossbreeding), resulting in a new pure line gathering favorable alleles present in two or more genotypes. The material resulting from these processes can be used by rural producers as a new cultivar.

It is known that the success of a new variety depends on the choice of germplasm, of a good crossbreeding block planning to be used by the breeder to attain the desired objectives, in addition to the selection of parents. It is also known that there is a need to know the type of trait inheritance so as to rationalize the cultivar development process (Arias, C. A. A. et al. Melhoramento e Biotecnologia: ferrugem da soja. In: IV Brazilian Soybean Congress held on June 5-8, 2006. Londrina (Proceedings)). The ability to predict the inheritance that certain traits will provide is essential in agriculture. Traits controlled by a single gene show results expected by Mendel's principles. However, traits controlled by more than one locus may differ from the expected results. Statistic methods and experimental projects are created in order to predict the inheritance of several quantitative traits related to phenotypic traits.

In conducting segregating generations, several methods are used, among which are the Bulk Method, SSD (Single Seed Descent) and backcrossing. In the bulk method, segregating generations, generally F2 and F5, are grown with the seeding and harvest of all the plants mixed in a single population. Therefore, in the bulk method, the seeds used for growing each segregating generation are a sample of the seeds harvested in the previous generation. After five generations of self-fertilizing crops, the plants exhibit a high degree of homozygosis and can be selected for individual harvest (Souza, A. P. Biologia Molecular Aplicada ao Melhoramento. In: Recursos Genéticos e Melhoramento—Plantas. Luciano L. Nass; Afonso C. C. Valois; Itamar S. de Melo; Maria Clélia Valadares-Inglis. (Org.) 1ª. Ed. Rondonópolis, 2001, v. 1, p 939-966.

The SSD method in soybean was described by Brim (1966) (Brim, C. A.; 1966. A modified pedigree method of selection in soybeans. Crop Science, v. 6, p. 20) and consists of segregating generation advancement (from F2 to F5) harvesting a single pod (2 to 3 seeds) from each plant; however, only one plant from each pod is used to grow the next generation. A sample is harvested and conserved. In his way, at the end of the process, each line corresponds to a different F2 plant and, therefore, there is a reduction in the loss caused by deficient sampling or natural selection.

Backcrossing is not exactly a method for growing segregating populations. It is a strategy used to improve the phenotypic expression of a deficient trait, especially if this trait is of a qualitative inheritance. The use enables the transfer of a gene or of a few genes from a parent called donor parent (DP) to another parent called recurrent parent (RP), and the recurrent parent is usually a cultivar of commercial interest having some kind of deficiency in its cultivation that needs to be improved. This deficiency can be corrected by the process of transferring the gene from the donor parent, which does not have the deficiency, to the recurrent parent. This procedure, that is to say, the cross of individuals from the segregating population with the recurring parent, is called backcrossing and is responsible for recovering almost 100% of the recurring parent genotype (Souza, A. P. Biologia Molecular Aplicada ao Melhoramento. In: Recursos Genéticos e Melhoramento—Plantas. Luciano L. Nass; Afonso C. C. Valois; Itamar S. de Melo; Maria Clélia Valadares-Inglis. (Org.) 1ª. Ed. Rondonópolis, 2001, v. 1, p 939-966).

In the end of the selective process, the breeder identifies one or a few pure lines with superior traits that will originate a new cultivar.

It is important to point out that in terms of improvement aiming at disease and pest resistance, gene pyramiding is recommended. Pyramiding relates to the association of several resistance genes present in a same cultivar aiming at obtaining a lasting and broad-spectrum resistance (Kelly, J. D.; Gepts, P.; Miklas, P. N.; Coyne, D. P. Tagging and mapping of genes and QTL and molecular marker-assisted selection for traits of economic importance in bean and cowpea. Field Crops Research, v. 82, p. 135-154, 2003).

However, in practice, the pyramiding of resistance genes or even rust tolerance (ASR) is difficult because the breeder cannot visually distinguish the plants with one or more resistance or tolerance genes, since phenotypically they have the same kind of reaction, that is, RB lesions.

In this context, biotechnology arose as a tool to facilitate and accelerate research in widely different areas, in particular genetics and improvement. The use of molecular markers is an effective and rapid strategy in the identification and transfer of new genes (Tanskley S. D. (1983). Molecular markers in plant breeding. Plant Molecular Biology Rep. 1: 3-8; Tanskley, S. D., McCouch S. R. (1997) Seed banks and molecular maps: unlocking genetic potential from the wild. Science v. 277: 1063-1066.). Molecular markers can be used in improvement programs directed to selecting qualitative and quantitative traits.

It is known that molecular markers appeared as a huge contribution from the development of molecular techniques that enable genome analysis. Molecular markers can have many uses in plants, being especially utilized in gene mapping and QTLs ("Quantitative Trait Loci") of interest. Song et al. (2004) (Song, Q. J., Marek, L. F., Shoemaker, R. C., Lark, K. G., Concibido, V. C., Delannay, X., Specht, J. E., Cregan, P. B. (2004). A new integrated genetic linkage map of the soybean. Theoretical and Applied Genetics, v. 109, p. 122-128), have developed a dense soybean linkage map, and it is known that the association of genes with molecular markers in soybean is being widely used.

The following examples of molecular markers can be mentioned: isoenzyme electrophoresis, "Restriction Fragment Length Polymorphisms" (RFLPs), "Random Amplified Polymorphic DNAs" (RAPDs), "Arbitrarily Primed Polymerase Chain Reaction" (AP-PCR), "DNA Amplification Fingerprinting" (DAF), "Sequence Characterized Amplified Regions" (SCARs), "Amplified Fragment Length Polymorphisms" (AFLPs), "Simple Sequence Repeats" (SSRs) and "Single Nucleotide Polymorphisms" (SNPs). Among the molecular markers cited above, SSRs are of interest for genetic mapping because each marker corresponds to a single position in the genome, but has several alleles yielding a high degree of polymorphism (Cregan P. B., Jarvik, T., Bush, A. L., Shoemaker, R. C., Lark, K. G., Kahler, A. L., Kaya, N., VanToai, T. T., Lohnes D. G., Chung, J., Specht, J. E. (1999). An integrated genetic linkage map of the soybean genome. Crop Science, v. 39: 1464-1490). Furthermore, they are easy-to-use, yield consistent results and are accessible to almost all biotechnology labs.

The construction of a genetic map requires the definition of the types of markers to be mapped and the type of genetic delineation to be used to detect the existing linkage disequilibrium among them. The several types of genetic delineations that can be used to construct the genetic map of plant species have in common the yield of generations showing linkage disequilibrium for segregating loci, enabling linkage analysis. Several factors are responsible for linkage disequilibrium, among them genetic selection and derivation. However, in segregating generations derived from crossings between lines (for instance, generation F2 and backcrossing), the main cause for this is related to the physical linkage of the loci, having been the genetic basis of the classical linkage analysis constructed. Due to the physical linkage of the loci, linkage disequilibrium is elevated in the populations derived from controlled crosses and, consequently, the ability to detect the linkage between two physically linked loci is also high. Therefore, the suitable choice of parent materials is essential in the first stage of the process (Coelho, A. S. G. e Silva, H. D. "Construção de Mapas Genéticos & Mapeamento de QTL's". Piracicaba, SP-February, 2002. 66 p).

After these steps, linkage analysis is carried out with a view to generate a genetic map involving an assessment of the segregation pattern of individual markers, the detection of the linkage disequilibrium between pairs of markers, the measuring of the distance between markers and the ordering of markers in linear linkage groups. The phenotypical class for which the gene is responsible is also considered a marker;

however, it is a morphological marker, rather than a molecular marker (Coelho, A. S. G e Silva, H. D. 2002—cited above).

According to the same authors, the detection of the linkage between the loci is performed based on the $X^2$ adherence test, which is based on the comparison between the frequencies observed in the different genotypic classes and those expected under the independent segregation condition between loci. This test provides an estimate of the likelihood of observed deviations given the independence condition. The 5% likelihood level is the critical point for rejecting the independence hypothesis. In the conditions wherein the likelihood of deviations found, given the independence condition, was lower than 5%, the hypothesis was rejected and it is considered that the loci are not independently segregating, that is, they are linked.

In the present invention, as there already is a soybean consensus linkage map, gene-linked markers were identified through the BSA (Bulked Segregant Analysis) method. The BSA method, proposed by Michelmore et al. (1991), (Michelmore, R. W., Paran, I., Kessell, R. V. (1991). Identification of markers linked to disease-resistance genes by bulked segregant analysis: A rapid method to detect markers in specific genomic regions by using segregating populations. Proceedings of National Academy of Science of USA, v. 88, p. 9828) is a quick and efficient strategy for identifying the link between molecular markers and qualitative traits. By using this technique, individuals from a F2 population segregating for 2 alleles of a single gene are grouped in 2 bulks of contrasting homozygous genotypes. Since the division of bulks is made taking into account only the trait of interest, all the other genes are randomly grouped. Thus, the genetic background becomes equal between the 2 groups and they only differ in the selected region. As a consequence, a polymorphic marker between the contrasting parents having the same polymorphism between the 2 bulks is very likely to be associated with the gene of interest. The authors emphasize that the markers need to be closer than 15 cM from the locus of interest to be effective, because at this distance, even if recombination occurs, the marker and the gene tend to remain together. However, the threshold distance for detecting the linkage seems to be 25 cM.

For the construction of bulks, the minimum number of individuals used is determined by the frequency with which polymorphism of markers unlinked to the gene of interest is expected to be found between the bulks, and this is reflected in the type of marker used (dominant or codominant). For the dominant marker, for instance, the likelihood of a bulk of n individuals having a band and a second bulk with the same number of individuals not having this band is $2(1-[1/4^n])(1/4)^n$ when the marker is unlinked to the target gene. That is, for 2 contrasting bulks of 10 individuals, the probability of a marker unlinked to the target gene being polymorphic between 2 bulks is of $2 \times 10^{-6}$. Therefore, with a few individuals in each bulk and even when several markers are used, the chances of detecting unlinked markers are small (Michelmore, R. W., Paran, I., Kessell, R. V. (1991).

Mapmaker (Lander E S.; Green, P.; Abrahamson, J.; Barlow, A.; Daly, M. J.; Lincoln, S. E.; Newburg, L. (1987). Mapmaker: an interactive computer package for constructing genetic linkage maps of experimental and natural populations. Genomics, v. 1, p. 174-181) is an interactive software for constructing genetic linkage maps. The program uses an efficient algorithm to carry out multipoint linkage analyses (which is a simultaneous estimate of all the recombination fractions in the data) of several loci, working with dominant, recessive or codominant molecular markers. The data used can originate from backcrossing, F2 or F3 populations resulting from interbreeding and recombinant inbred lines. The distances between the loci are calculated using likelihood.

The construction of linkage maps is hampered by genotyping errors. Low error rates cause an expansion of the map and interfere in determining the correct gene order. That is why the current version of MapMaker/EXP 3.0 (Lincoln, S. E., Lander, S. L. (1993). Mapmaker/exp 3.0 and Mapmaker/QTL 1.1 Whitehead Inst. Of Med Res. Tech Report. Cambridge, Mass.) incorporated an algorithm for detecting potential genotyping errors (Lincoln, S. E.; Lander, S. L. (1992) Systematic detection of errors in genetic linkage data. Genomics, v. 14, p. 604-610). The method detects the majority of errors and with this function it is possible to construct accurate maps.

In the screening process for disease resistance, especially when the pathosystems are difficult to work with due to maintenance difficulties, isolation and pathogen inoculation, or in the disease assessment process, the use of molecular markers is highly recommended. This is the case with Asian soybean rust. It is known that molecular markers detect the genetic information without environmental interference. Another aspect to be considered is the detection of variations in the nucleotide sequence and even in the nontranscribed regions. In this way, it is possible to eliminate and relieve the need to use work-intensive phytopathological processes, identifying individuals from a segregating population carrying the marker linked to the favorable allele of interest, resulting in time and resource savings.

Within this context, the present invention is a significant contribution to improvment programs directed to the use of molecular marker assisted screening, using molecular markers linked to disease-resistant genes, particularly resistant to Asian soybean rust. These markers help to position genes related with disease resistance in the soybean linkage map, for instance.

Asian soybean rust (ASR), caused by fungus *Phakopsora pachyrhizi*, is considered the most destructive soybean leaf disease (Miles, M. R.; Frederick, R D.; Hartman, G. (2003) Soybean rust: Is the U.S. soybean crop at risk? Online. APSnet Feature, American Phytopathological Society). The disease spreads through uredospores and has the potential of causing severe damages to soybean crops.

Discovered in Japan in 1902, it has spread to Asia and Australia in 1934, (Kochman, J. K. (1977). Soybean rust in Australia. Pp. 44-48 In: Rust of Soybean—The problem and research needs. R. E. Ford and J. B. Sinclair, eds. International Agricultural Publications, Manila, The Philippines), India in 1951 (Sharma, N. D.; Mehta, S. K. (1996). Soybean rust in Madhya Pradesh. Acta Botanica Indica, v. 24: 115-116), Hawaii in 1994 (Killgore, E.; Heu, R. (1994). First report of soybean rust in Hawaii. Plant Disease, v. 78: 1216), and Africa in 1996 (Akinsanmi, O. A.; Ladipo, J. L.; Oyekan, P. O. (2001). First report of soybean rust (*Phakopsora pachyrhizi*) in Nigeria. Plant Disease, v. 85, p. 97). In South America, the disease was reported for the first time in 2001 in Paraguay (Morel, W.; Yorinori, J. T. (2002). Situacion de la roja de la soja em el Paraguay. Bol de Divulgacion No. 44. Ministério da Agricultura y Granaderia, Centro Regional de Investigacion Agrícola, Capitan Miranda, Paraguay) and in the following years it arrived in Brazil, Argentina, Bolivia and Colombia (Rossi, R. L. (2003). First report of *Phakospora pachrhizi*, the casual organism of soybean rust in the Provence of Misiones, Argentina. Plant Disease, v. 87: 102; Yorinori, J. T.; Lazzarotto, J. J. (2004). Situação da ferrugem asiática da soja no Brasil e na América do Sul. In: Documentos/Embrapa Soja, no. 236, Londrina). In these countries, the losses in productivity due to Asian soybean rust were drastic, varying from 10% to 80% in some crops (Yorinori J T (2004) Ferrugem "asiática" da soja no Brasil: evolução, importância econômica e controle. In: Junior J N, Lazzarotto J J (eds) Documentos 247. Embrapa, Londrina, Brazil, 36 p. In the United States, the first symptoms of the disease were reported in November, 2004 (Schneider, R. W.; Hollier, C. A.; Hitam, H. K. (2005). First report of soybean rust caused by *Phakopsora pachyrhizi* in the continental United States. Plant Disease, v. 89: 774), and, in 2005, yield loss was estimated to be up to 50% (Dorrance, A. E.; Draper, M. A.; Hershman, D. E., eds. Using Foliar Fungicides to Manage Soybean Rust. NC-504 Land Grant Universities Cooperating. Bulletin SR-2005). However, due to unfavorable environmental conditions for the pathogen, the disease did not achieve the expected levels (Sconyers, L. E.; Kemerait, R. C.; Brock, J.; Phillips, D. V.; Jost, P. H.; Sikora, E. J.; Gutierrez-Estrada, A.; Muller, J. D.; Marois, J. J.; Wright, D. L.; Harmon, C. L. (2006). Asian soybean rust development in 2005: A perspective from the Southeastern United State Online. APSnet Feature, American Phytopathological Society).

The development of the fungus is favored by temperatures between 15° and 29° C. and high humidity. In favorable conditions, the symptoms can be detected in 5 to 8 days after the plant is infected by the uredospores (Marchett, M. A.; Melching, J. S.; Bromfield, K. R. (1976). The effects of temperature and dew period on germination and infection by uresdospores of *Phakopsora pachyrhizi*. Phytopathology, v. 66: 461-463; Melching, J. S.; Dowler, W. M.; Koogle, D. L.; Royer, M. H. (1989). Effects of duration, frequency, and temperature of leaf wetness periods on soybean rust. Plant Disease, v. 73: 117-122). In cultivated soybean, the first symptoms are light-brown polygonal lesions of 2 to 5 mm on the adaxial leaf surface. In the 10 to 14 days period, volcano-shaped lesions known as pustules appear on the abaxial surface of the leaf, where uredospores are produced (Marchett, M. A.; Uecker, F. A.; Bromfield, K. R. (1975). Uredial development of *Phakopsora pachyrhizi* in soybeans. Phytopathology, v. 65: 822-823.; Melching, J. S.; Dowler, W. M.; Koogle, D. L.; Royer, M. H. (1989). Effects of duration, frequency, and temperature of leaf wetness periods on soybean rust. Plant Disease, v. 73: 117-122). The effects of temperature and dew period on germination and infection by uresdospores of *Phakopsora pachyrhizi*. Phytopathology, v. 66: 461-463; Melching, J. S.; Dowler, W. M.; Koogle, D. L.; Royer, M. H. (1989). Effects of duration, frequency, and temperature of leaf wetness periods on soybean rust. Plant Disease, v. 73: 117-122). As the infection increases, severe lesions and premature defoliation occur in the plants.

Although fungicides minimize losses, the use of resistant or tolerant cultivars is the best alternative for controlling the disease, in order to reduce costs, facilitate management and help in environmental conservation. It is known that fungus resistance naturally occurs in genotypes of the *Glycine* genus (Burdon, J. J.; Marshall, D. R. (1981). Evaluation of Australian native species of *Glycine canescens*, a wild relative of soybean. Theoretical Applied Genetics, v. 65: 44-45; Burdon, J. J. (1988). Major gene resistance to *Pha kopsora pachirhizi* in *Glycine canescens*, a wild relative of soybean. Theoretical Applied Genetis, v. 75: 923-928), and is typically conferred by the hypersensitivity reaction. This is a common type of immune response caused by the presence of resistance genes (R-gene) of the plant when challenged by pathogen avirulence genes (Avr-genes) (McDowell, J. M.; Simon, S. A. (2006). Recent insights into R gene evolution. Molecular Plant Pathology, v. 7: 437-448). In this sense, resistant genotypes show a reddish-brown (RB) lesion with no or little sporulation, while susceptible genotypes show a light-brown (TAN) lesion and profuse sporulation.

During the process for the development of a ASR-resistant or -tolerant soybean variety, the plants have to be assessed at each generation as to their level of resistance or tolerance to the pathogen, thus identifying the resistant or tolerant plants at each cycle, until the superior cultivar is selected. In practice, the infection process occurs naturally when the fungi spores are in the air or artificially by spraying the leaves with a spore solution collected from previously infected plants. Natural occurrence is cyclic and very dependent on climate conditions. Furthermore, the breeder not always has available spores to promote artificial inoculations. The reasons range from technical difficulties to keeping the infected plants and legal prohibitions. This difficulty is more pronounced when trying to develop resistant cultivars in countries where the disease has not occurred yet and where the pest is still quarantinable.

Cultivated soybean (*Glycine max*) has four qualitative dominant resistance genes. Rpp1 identified in PI 200492 ((McLean, R. J.; Byth, D. E. (1980). Inheritance of resistance to rust (*Phakopsora pachyrhizi*) in soybean. Australian Journal Agricultural Research, v. 31: 951-956); Rpp2 na PI 230970 (Bromfield, K. R.; Hartwig, E. E. (1980). Resistance to soybean rust and mode of inheritance. Crop Science, v. 20, n. 2, p. 254-255); Rpp3 in PI 462312 (Bromfield, K R.; Melching, J. S. (1982). Sources of specific resistance to soybean rust. (Abstr.) Phytopathology, v. 72, p. 706), and Rpp4 in PI 459025 (Hartwig, E. E. (1986). Identification of a fourth major gene conferring to resistance to soybean rust. Crop Science, v. 26, p. 1135-1136). The resistance presented by each gene is limited to the specific pathogen variety (Bonde, M. R.; Nester, S. E.; Austin, C. N.; Stone, C. L.; Frederick, R D.; Hartman, G. L.; Miles, M. R. (2006). Evaluation of virulence of *Phakopsora pachyrhizi* and *P. meibomiae* isolates. Plant Disease, v. 90, p. 708-716.) and this resistance can be overcome in a short period of time due to the coevolution of host resistance and pathogen virulence (McDonald, B. A.; Celeste, L. (2002). Pathogen population genetics, evolutionary potential, and durable resistance. Annual Ver. Phytopathology, v. 40, p. 349-379). Additionally, the fungus has different varieties with variable geographic distribution. Therefore, it is impossible, for instance, to ensure that an ASR-resistant or -tolerant cultivar selected with spores produced under field conditions in the USA will be resistant or tolerant when cultivated under field conditions in Brazil.

In 2002, the resistance provided by the FT-2 cultivar and the four ASR-resistance genes were previously reported in Brazil as being effective (Arias, C. A. A.; Brogin, R. L.; Yorinori, J. T.; Kiihl, R. A. de S.; Toledo, J. F. F. (2003). Um gene dominante determinando a resistência da cultivar FT-2 à ferrugem da soja (*Phakopsora pachyrhizi* Sydow). In: Congresso Brasileiro de Melhoramento de Plantas, 2; Porto Seguro, 2003. Proceedings. Porto Seguro: Sociedade Brasileira de Melhoramento de Plantas—SBMP—(Compact disc)). However, in the next harvest, the Rpp1, Rpp3 and FT-2 resistance was simultaneously broken ((Yorinori, J. T. (2004). Ferrugem "asiática" da soja no Brasil: evolução, importância econômica e controle. Yorinori, J. T. et al. (eds)—Londrina: Embrapa Soja, 2004, 36 p. (Documentos, 27)). Thus, the efforts to control ASR with the use of resistant cultivars carrying single genes have not yet proved to be successful. Therefore, the identification and use of new disease resistance sources are pursued by the genetic improvement programs carried out by geneticists and soybean breeders, and are essential for those who are involved with soybean.

In view of the foregoing, the importance of the present invention is clear as a highly applicable methodology to help in the control of ASR, facilitating and accelerating the development of disease-resistant or -tolerant cultivars. The present invention solves the problem of the diversity in varieties and the geographic distribution of the pathogen because it enables the selection to be made in the absence of the pathogen by analyzing DNA polymorphic markers linked to rust resistance or tolerance alleles.

The present invention discloses the identification of five new sources of ASR resistance by means of genetic analyses. There are two cases with dominant resistance (PI 200487 and PI 200526), in two of the sources, resistance is recessive (PI 200456 e PI 224270) and, in the other, resistance has incomplete dominance (PI 471904). It is the first case of ASR resistance conditioned by a recessive gene/allele.

In addition, the present invention also uses SSR molecular markers from the soybean linkage map to construct the genetic map of the genes of these new sources, as well as the map of the genes present in the original sources of Rpp2 (PI 230970) and Rpp4 (PI 459025).

The present invention enables the association of resistance or tolerance genes, because it identifies not only new loci and alleles associated with these loci, but also DNA segments linked to said loci that can be easily tracked during the genetic improvement process, regardless of the improvement method used by the breeder (SSD, Bulk, Backcrossing, etc.), using routine DNA analysis techniques.

In the context of the present invention, the association of disease-resistance or tolerance genes with molecular markers will render positional cloning possible (Kilian, A.; Chen, J.; Han, F.; Steffenson, B.; Kleinhofs, A. (1997). Towards map-based cloning of the barley stem rust resistance genes Rpg1 and Rpg4 using rice as an intergenomic cloning vehicle. Plant Molecular Biology, v. 35, p. 187-195; Yahiaoui, N.; Srichumpa, P.; Dudler, R.; Keller, B. (2004). Genome analysis at different ploidy levels allows cloning of the powdery mildew resistance gene Pm3b from hexaploid wheat. Plant Journal, v. 37, p. 528-538), and with cloning, the strucutre, organization and operation of genes can be better understood (Yan, P.; Chen, X. M. (2006). Molecular mapping of a recessive gene for resistance to stripe rust in barley. Theoretic Applied Genetics, v. 113, p. 529-537). Furthermore, this association enables the molecular marker-assisted screening to indirectly identify individuals in segregating populations (Kelly, J. D.; Gepts, P.; Miklas, R N.; Coyne, D. P. (2003). Tagging and mapping of genes and QTL and molecular marker-assisted selection for traits of economic importance in bean and cowpea. Field Crops Research, v. 82, p. 135-154) carrying the favorable allele under selection, resulting in time and resource savings.

The methods of the present invention are also extremely important in backcrossing, accelerating the recovery of recurrent genotypes. It also enables the understanding of genome evolution and the different relationships between the different genes.

Furthermore, with the data provided by the present invention the gene pyramiding process will be facilitated. Gene pyramiding is a work-intensive process due to the difficulty in identifying the presence of multiple genes, since selection is done phenotypically, via the analysis of symptoms. Using molecular markers linked to the genes to be pyramided, it will be possible to monitor the genes introduced during the process (Alzate-Marin, A. L.; Cervigni, G. D. L.; Moreira, M. A. (2005). Marker-assisted selection in the development of disease resistant plants, with emphasis on common bean and soybean. Fitopatologia Brasileira, v. 30, n. 4, p. 333-342).

Definitions

The definitions below are included in order to clarify certain terms used in the scope of the invention so as to facilitate understanding:

Alleles: One or more alternative forms of a gene.

Chromosome: a discrete unit of the genome carrying many genes. Each chromosome consists of a very long molecule of duplex DNA and an approximately equal mass of proteins. It is visible as a morphological entity only during cell division.

Artificial crossing: A crossing to introduce a new genetic material into a plant with a view to develop a new variety.

Test cross: involves crossing of an unknown genotype to a recessive homozygote so that the phenotype of the progeny corresponds directly to the chromosomes carried by the parents of unknown genotype.

Gene Map Distance: measured in cM (centimorgans)=percentage recombination (sometimes subject to adjustments).

Divergence: the percent difference in the nucleotide sequence between two related DNA sequences or in the amino acid sequence between two proteins.

Gene: (cistron) a segment of DNA that is involved in producing a RNA molecule that can be translated into a polypeptide chain; it also includes regions preceding and following the coding region (leader and trailer) as well as intervening sequences (introns) between individual coding segments (exons).

Genotype: the genetic constitution of a cell or organism.

F1 Generation: The first filial generation, produced by crossing two parental lines (homozygotes).

Linkage group: includes all gene loci that can be linked (directly or indirectly) by linkage relations; can be equivalent to a chromosome.

Heterozygote: an individual that has different alleles at a particular gene locus.

Homozygote: an individual that has the same alleles at a particular gene locus on homologous chromosomes.

Linkage: the tendency of some genes to be inherited together. It is the result of the location of genes on the same chromosome and is measured by the recombination among the loci.

Locus: the position on a chromosome that is occupied by a specific gene with a given trait; a locus can be also be occupied by any of the alleles of the gene.

Genetic map: map which shows the relative positions of gene loci forming the genome of an organism. The map is determined based on the joint inheritance of the loci. The distances among loci are calculated by their recombination frequency and are measured in cM.

Marker, Molecular Marker, Nucleic Acid Marker: relates to a nucleotide sequence used as a reference point that identifies a genetically linked locus. A marker can be derived from the genomic nucleotide sequence or from expressed nucleotide sequences (such as, for instance, from cDNA). In the context of this invention, this term can be associated with a specific marker or another gene locus (for instance, a locus related to disease resistance), wherein the marker pair or the marker and the second locus are genetically linked in the same linkage group; therefore, they are in linkage disequilibrium. In this respect, linkage disequilibrium is defined as any deviation from the frequencies expected independently, indicating the existence of an association among loci. Therefore, for the molecular markers to contribute to the inheritance and improvement studies, the population needs to be in linkage disequilibrium, otherwise the probability of a specific class of marker occurring would be independent of the segregation of the alleles of a given gene or QTL of interest, for instance.

Improvement: science directed to the genetic modification of living organisms.

Pathogen: organism that causes disease, infectious agent.

PI—Plant Introduction: plant genotype incorporated into any region different from its primary origin center.

Gene pyramiding: relates to the accumulation of two or more genes that yield the phenotype of interest in elite genotypes, either by classical improvement methods or by transformation.

Polymorphism: relates to the simultaneous occurrence in the population of genomes having allelic variations (such as alleles that yield different phenotypes or—for instance—the difference in the size of the sequences of certain microsatellites).

Tandem Repeats: multiple copies of the same sequence arranged in series.

Disease Resistance: genetic ability to prevent infection by a pathogen. Some forms of resistance operate by pathogen exclusion, some la preventing pathogen spread, and some by tolerating pathogen toxin; ability to resist to abiotic or biotic factors.

Backcrossing: a crossing of an individual with one of its parents. The descendants are called backcrossing generation or progeny.

Screening: describes the use of certain conditions to enable the survival of cells having a certain phenotype.

Susceptible: incapable of resisting to or tolerating damages caused by biotic or abiotic stress.

Tolerant: organism (plant) having the ability to live with a pathogen.

BRIEF DESCRIPTION OF DRAWINGS

FIG. 1.A shows the soybean linkage map for group G and FIG. 1.B shows the F2 population map resulting from PI459025 X Coodetec 208.

FIG. 2.A shows the soybean linkage map for group J and FIG. 2.B shows the F2 population map resulting from the cross between 224270 X Coodetec 208.

FIG. 3.A shows the soybean linkage map for group N and FIG. 3.B shows the F2 population map resulting from the cross between 200456 X Coodetec 208; FIG. 3.C shows the map resulting from the cross between PI 471904 (Orba) X Coodetec 208, which resulted in a F2 population. FIG. 3.D represents the map from F2 resulting from the cross between PI 200526 X Coodetec 208.

DETAILED DESCRIPTION OF THE INVENTION

The present invention relates to methods for identifying and using genetic markers, more specifically soybean genetic markers, and particularly markers which are linked to disease resistance or tolerance loci, such as, for example, Asian soybean rust-resistant or -tolerant loci, in different species of the *Glycine* genus.

An embodiment of the present invention relates to a method of identifying and selecting individuals having a phenotypic trait of interest from a biological population, particularly a plant population, comprising:

(a) associating a molecular marker with a phenotypic trait of interest;

(b) segregating individuals from the biological population based on the presence or absence of at least one molecular marker associated with said phenotypic trait, wherein said phenotypic trait is attributable to one or more genetic loci;

(c) indicating the markers which show the profile of the segregating individuals of (b); and (d) determining the patterns of the markers of (c) the genetic loci associated with the phenotypic trait of interest.

Preferably, a plant population of the *Glycine* genus may be used, particularly from the *Glycine max* species, comprising at least 11 individuals.

The phenotypic trait of interest may be productivity and resistance and/or tolerance to diseases, particularly to Asian soybean rust, and is attributable to a locus or QTL.

The molecular marker may be a fragment of DNA, cDNA or RNA having at least slight variations in the nucleotide sequences between the individuals of the biological population. Preferably, the marker is selected from RFLPs, RAPDs, AFLPs, SSRs, SNPs, ESTs and RGA probes, and is positioned in a region of a linkage group. Preferably, the molecular marker is any marker mapped at 10 cM or less from the locus or QTL of the phenotypic trait of interest.

The linkage group represents all the loci which may be directly or indirectly connected by linkage relations. Particularly, the linkage group is part of a chromosome or a complete chromosome. It may be selected from the group consisting of linkage group G, linkage group J and linkage group N of the soybean consensus linkage map.

In a preferred embodiment, the linkage group is linkage group G of the soybean consensus linkage map and the molecular marker is one or more among Satt12, A816_1, A890_1, Sat_164, Satt503, Satt517, Sat_143, Mng273_2, Satt288, A121_2, A885_1, Satt612, K493_1, T005_2, bac1F11Rhnd and OP_M02a.

In another preferred modality, the linkage group is linkage group J of the soybean consensus linkage map and the molecular marker is one or more among Satt215, Sat_361, Sct_001, Sat_093, A109_9, Sat_366, Satt621, Satt620, Sat_350, RGA_3, RGA_2a, Satt244 and Satt431.

In another preferred embodiment, the linkage group is linkage group N of the soybean consensus linkage map and the molecular marker is one or more among A426_2, Sle_003, i4_2, Sat_084, Satt393, Satt584, Satt485, Sat_166, Sat_208, BLT049_1, Bng095_2, OP_F13, Satt125, Sat_275, Sle_3, RGA_6b, OP_U09b, mO128_1, Sat_280, Satt080 e Sat_266.

Preferably, the molecular markers are selected from the genotypes having different phenotypes, for example, from soybean genotypes PI 459025, PI 230970, PI 200456, PI 224270, PI 200526, PI 200487 and PI 471904 or from genotypes having Asian soybean rust resistance genes or even alleles of these PIs.

The identification of the molecular markers can be made by BSA linkage analysis followed by genetic mapping.

Another embodiment of the present invention relates to a method of pyramiding genes associated with phenotypic traits of interest in a plant population, particularly of the *Glycine* genus, preferably of the *Glycine max* species, comprising:

(a) associating one or more molecular markers to the phenotypic trait of interest in one or more plants or plant varieties;

(b) identifying the marker(s) for each gene to be incorporated in step (c);

(c) incorporating the genes from the plant population by crossbreeding between said plants or plant varieties; and (d) monitoring the incorporation of genes into the plant population through the marker(s).

Preferably, step (c) of this method consists of incorporating the largest possible number of favorable genes for a given trait of interest into a single genotype.

The phenotypic trait of interest may be productivity and resistance and/or tolerance to diseases, particularly to Asian soybean rust.

The molecular marker may be any marker mapped at 10 cM or less from the locus or QTL of the phenotypic trait of interest. It may be positioned in a region of a linkage group, such as linkage group G, linkage group J, and linkage group N of the soybean consensus linkage map.

In a preferred embodiment, the linkage group is linkage group G of the soybean consensus linkage map and the molecular marker is one or more among Satt12, A816_1, A890_1, Sat_164, Satt503, Satt517, Sat_143, Mng273_2, Satt288, A121_2, A885_1, Satt612, K493_1, T005_2, bac1F11Rhnd and OP_M02a.

In another preferred embodiment, the linkage group is linkage group J of the soybean consensus linkage map and the molecular marker is one or more among Satt215, Sat_361, Sct_001, Sat_093, A109_9, Sat_366, Satt621, Satt620, Sat_350, RGA_3, RGA_2a, Satt244 and Satt431.

In another preferred embodiment, the linkage group is linkage group N of the soybean consensus linkage map and the molecular marker is one or more among A426_2, Sle_003, i4_2, Sat_084, Satt393, Satt584, Satt485, Sat_166, Sat_208, BLT049_1, Bng095_2, OP_F13, Satt125, Sat_275, Sle_3, RGA_6b, OP_U09b, mO128_1, Sat_280, Satt080 and Sat_266.

The plants or plant varieties used may be selected, for example, from soybean genotypes PI 459025, PI 230970, PI 200456, PI 224270, PI 200526, PI 200487 and PI 471904, or from genotypes having Asian soybean rust resistance genes or even alleles of these PIs. Preferably, the soybean genotypes used are PI 200456, PI 224270, PI 200526, PI 471904 or alleles of these PIs. Particularly, the alleles are selected from between the rpp2 locus at linkage group J and the Rpp5/rpp5 locus at linkage group N of the soybean consensus linkage map.

Preferably, one or more among A426_2, Sle_003, i4_2, Sat_084, Satt393, Satt584, Satt485, Sat_166, Sat_208, BLT049_1, Bng095_2, OP_F13, Satt125, Sat_275, Sle_3, RGA_6b, OP_U09b, mO128_1, Sat_280, Satt080 and Sat_266 are used as markers for the Rpp5/rpp5 gene in the PI 200456, PI 200487 and PI 200526 genotypes. Preferably, one or more among Satt215, Sat_361, Sct_001, Sat_093, A109_9, Sat_366, Satt621, Satt620, Sat_350, RGA_3, RGA_2a, Satt244 and Satt431 are used as markers for the rpp2 gene in the PI 224270 genotype. Particularly, one or more among Satt12, A816_1, A890_1, Sat_164, Satt503, Satt517, Sat_143, Mng273_2, Satt288, A121_2, A885_1, Satt612, K493_1, T005_2, bac1F11Rhnd and OP_M02a are used as markers for the Rpp4 gene in the PI 459025 genotype.

An additional embodiment of the present invention relates to a method for isolating and identifying genes associated with phenotypic traits of interest in a plant population, particularly of the *Glycine* genus, preferably of the *Glycine max* species, by positional cloning, comprising:

(a) preparing a genomic library;

(b) selecting cloned fragments from said library by using molecular markers;

(c) using the selected cloned fragments to create a contig of cloned DNA inserts; and (d) identifying the gene(s) in one or more clones residing in the contig.

The phenotypic trait of interest may be productivity and resistance and/or tolerance to diseases, particularly to Asian soybean rust.

The molecular marker may be any marker mapped at 10 cM or less from the locus or QTL of the phenotypic trait of interest. It may be positioned in a region of a linkage group, such as linkage group G, linkage group J and linkage group N of the soybean consensus linkage map.

In a preferred embodiment, the linkage group is linkage group G of the soybean consensus linkage map and the molecular marker is one or more among Satt12, A816_1, A890_1, Sat_164, Satt503, Satt517, Sat_143, Mng273_2, Satt288, A121_2, A885_1, Satt612, K493_1, T005_2, bac1F11Rhnd and OP_M02a.

In another preferred embodiment, the linkage group is linkage group J of the soybean consensus linkage map and the molecular marker is one or more among Satt215, Sat_361, Sct_001, Sat_093, A109_9, Sat_366, Satt621, Satt620, Sat_350, RGA_3, RGA_2a, Satt244 and Satt431.

In another preferred embodiment, the linkage group is linkage group N of the soybean consensus linkage map and the molecular marker is one or more among A426_2, Sle_003, i4_2, Sat_084, Satt393, Satt584, Satt485, Sat_166, Sat_208, BLT049_1, Bng095_2, OP_F13, Satt125, Sat_275, Sle_3, RGA_6b, OP_U09b, mO128_1, Sat_280, Satt080 and Sat_266.

Preferably, the molecular marker is used for the Rpp5/rpp5 gene located at linkage group N of the soybean consensus linkage map. Contigs WmContig404, WmContig562, WmContig5258 or WmContig6713, or any contig having a marker closer than 5 cM from the gene may be used.

Another embodiment of the present invention relates to a method for obtaining cultivars, particularly a cultivar of the *Glycine* genus, preferably of the *Glycine max* species, which are resistant or tolerant to diseases, in particular to Asian soybean rust, comprising:

(a) hybridizing a source carrying one or more genes and/or alleles which are resistant or tolerant to a disease with a line or cultivar which is susceptible to said disease but agronomically adapted to the region for which the cultivar is to be obtained.

(b) generation advancement using at least one genetic improvement method;

(c) using at least one among the method of identification and selection as previously defined according to the present invention, the method of gene pyramiding as previously defined according to the present invention, and the method of isolation and identification of genes as previously defined according to the present invention to obtain the disease-resistant or -tolerant cultivar.

Preferably, the genetic improvement method of step (b) is selected from among "Bulk", SSD, MSSD and Backcrossing.

In a preferred embodiment, the source carrying one or more genes and/or alleles which are resistant or tolerant to a disease used in step (a) is PI 635026 and the line susceptible to the disease is TMGLM-3219.

In another preferred embodiment, the cultivar obtained is selected from CB06-953, CB06-954, CB06-955, CB06-956, CB06-957, CB06-958, CB06-959, CB06-960, CB06-961, CB06-962, CB06-963 and CB06-964.

Another embodiment of the present invention relates to a process for obtaining a plant population having a phenotypic trait of interest, comprising at least one among the method of identification and selection as previously defined according to the present invention, the method of gene pyramiding as previously defined according to the present invention, the method of isolation and identification of genes as previously defined according to the present invention and the method for obtaining disease-resistant or -tolerant cultivars as previously defined according to the present invention. The present invention also relates to the plant population obtained by said process. It should be understood that "plant population" comprises seeds, grains, shoots, cultivars, adult plants or any other component of the Plantae Kingdom.

The present invention relates to the use of soybean genotypes PI 459025, PI 230970, PI 200456, PI 224270, PI 200526, PI 200487 and PI 471904 as a source of a phenotypic trait of interest in the process for obtaining a plant population having a phenotypic trait of interest according to the present invention. The phenotypic trait of interest may be productivity and resistance and/or tolerance to diseases, particularly to Asian soybean rust.

Preferably, soybean genotypes PI 200456, PI 224270, PI 200456, PI 200526 and PI 471904 or PIs having the resistance or tolerance gene at the same loci as them.

An additional embodiment of the present invention relates to a method for controlling diseases, in particular Asian soybean rust, in a plant population, particularly of the *Glycine* genus, preferably of the *Glycine max* species, comprising genetically controlling the disease by using at least one among the method of identification and selection as previously defined according to the present invention, the method of gene pyramiding as previously defined according to the present invention, the method of isolation and identification of genes as previously defined according to the present invention and the method for obtaining disease-resistant or -tolerant cultivars as previously defined according to the present invention.

Preferably, the method further comprises chemically controlling the disease by applying at least one fungicide to the plant population. In particular, the fungicide is selected from among triazoles, strobilurins, benzimidazoles, prothioconazole, protilcnazole and mixtures thereof.

EXAMPLES

The examples below are merely illustrative and non-limiting.

Example 1

Genetic Improvement

Improvement with Molecular Markers

Material—Plant

The assays were carried out in a greenhouse, with controlled temperature and humidity. 48 ASR-resistant genotypes were selected. Homozygosis tests for resistance in different genotypes were carried out and 7 genotypes were selected, among which PIs 200487, 200526 and 471904. The source of the Rpp2 gene (PI 230970), of the Rpp4 gene (PI 459025) and PI 200456 and PI 224270, which carry recessive resistance genes, were also used in the present invention. Populations used in the work were obtained from the crossbreeding of each of the sources of resistance with the susceptible cultivar Coodetec 208, used as female parent, but not limited to said cultivar.

Self-fertilization of F1 plants. About 200 F2 plants resulting from each crossbreeding were assessed as to ASR-resistance. A $F_{2:3}$ progeny test was carried out to confirm the phenotype and determine the genotype of the F2 plants. The formula $n=\log(1-P)/\log(1-p)$ required 11 plants for each progeny, providing a confidence level of P 0.95 that the least probable event (p 0.25) would occur at least once. Germination problems required 20 seeds to be planted and only the progenies with 11 or more plants were assessed. Thus, about 180 F2 plants from each population were characterized. The data obtained were used for a study of the genetic control of the disease and for the formulation of hypotheses. Chi-square test was used to verify whether the proportions observed did not differ significantly from the ones expected. For the molecular analyses, only the characterized F2 plants were used.

Resistance Test—*Phakopsora pachyrhizi*

Phenotypic data on the F2 and $F_{2:3}$ populations were obtained by inoculating the individuals in vegetative stage V3/V4 with varieties of the *Phakopsora pachyrhizi* fungus. The uredospores were collected from the susceptible cultivar FMT-Bacuri, kept in a greenhouse, by washing the abaxial surface of the infected leaves and suspending the material in distilled water containing tween 20 (0.1 mL/L). The resulting solution was adjusted to the concentration of $50\times10^3$ uredospores/mL and manually sprayed over the plants. This procedure was carried out at sunset. The inoculated plants were kept under a temperature of 25° C./20° C.±3° C. day/night and natural lighting. Approximately 14 days after inoculation, when the symptoms of the disease were evident, the plants were assessed as to the lesion type (RB or TAN). Once the assessments had been made, the control of the disease was carried out by applying the fungicide IMPACT®.

DNA Extraction

Leaf tissue, free of any lesions, was collected from the parents and from all the F2 plants. The tissue was frozen in liquid nitrogen, lyophilized and ground into a fine powder, which was stored in a cold chamber until the DNA extractions were carried out. The DNA extraction was based on the protocol proposed by Saghai-Maroof et al. (1984) (Saghai-Maroof, M. A.; Soliman, K. M.; Jorgensen, R. A.; Allard, R. W. (1984). Ribosomal DNA spacer-length polymorphisms in barley: Mendelian inheritance, chromosomal locations, and population dynamics. Proceedings of the National Academy of Sciences of the United States of America, v. 81, p. 8014-8018), with a few modifications.

Analyses of Markers

The analyses with the SSR markers were carried out in 3 stages. A screening was previously carried out for polymorphism between the parents by using 190 pairs of SSR primers selected from the soybean linkage map published by Song et al. (2004) (Song, Q. J.; Marek, L. F.; Schoemaker, R. C.; Lark, K G.; Concibido, V. C.; Delannay, X.; Specht, J. E.; Cregan, P. B. (2004). A new integrated genetic linkage map of the soybean. Theoretical and Applied Genetics, v. 109, p. 122-128). The markers obtained are uniformly distributed among the 20 soybean linkage groups, covering the whole genome. The sequence for each primer was obtained from the website http://www.sovbase.org.

The evidence of the link between the SSR markers and resistance was verified by the bulked segregant analysis (BSA) proposed by Michelmore et al. (1991) (Milchelmore, R. W.; Paran, I.; Kessell, R. V. (1991). Identification of markers linked to disease-resistance genes by bulked segregant analysis: A rapid method to detect markers in specific genomic regions by using segregating populations. Proceedings of the National Academy of Sciences of the United States of America, v. 88, p. 9828-98-32). Two bulks were prepared for each of the 7 F2 populations, by combining identical DNA samples from 10 resistant individuals and 10 susceptible individuals. A screening of the bulks was carried out by using the polymorphic primers between the parents from each population. If the same pattern of polymorphism observed between the parents was evidenced in the bulks, the marker was considered to be linked and the region of the gene of each population was thus delimited. New SSR markers existing in the region of each gene were tested for polymorphism and used for the screening of all the individuals of the corresponding F2 populations, which were characterized by the $F_{2:3}$ progeny test.

The PCR used for the amplification of the microsatellite loci (SSR) for polymorphism analysis between parents and for BSA, and for the screening of individuals, were carried out in PTC-200 thermal cycler (MJ Research), with a final reaction volume of 20 µL, containing 30 ng of DNA template, 0.25 uM of each primer, 0.15 uM of each dNTP, 1.5 U of TAQ DNA polymerase, 2.5 mM of $MgCl_2$ and 1×PCR buffer. The amplification program used was as follows: 1 cycle of 95° C. for 3 min followed by 35 cycles of 94° C. for 30 s, 55-60° C. (depending on each primer's TM) for 30 s and 72° C. for 45 s and a final cycle of 72° C. for 10 min. The PCR products were separated in MetaPhor® agarose gel (Lonza Bioscience Switzerland) at 3% or 4%, depending on the size of the SSR fragment described in the map, and colored with ethidium bromide. The image acquisition was performed by Typhoon® scanner (Molecular Dynamics California, USA).

Linkage Analysis

Chi-square tests were carried out to determine whether the genotypic segregations of the SSR markers (microsatellites) used in the mapping did not significantly differ from what was expected. The construction of the linkage map was performed with the aid of the software MAPMAKER/EXP 3.0 (Lincoln, S. E.; Lander, S. L. (1993). Mapmaker/exp 3.0 and Mapmaker/QTL 1.1 Whitehead Inst. of Med. Res. Tech Report. Cambridge, Mass.), with the distances and order of the markers calculated using a LOD score of 3.0 and the Kosambi function with a maximum distance of 50 cM. The maps obtained were compared with soybean consensus linkage map.

Results

The results of the assessment of the present invention with regard to the genotypes exhibiting resistance are shown in table 01. This assessment is based on the type of lesion presented (RB—resistant and TAN—susceptible). The data presented by PI 459025, original source of Rpp4, confirm the presence of a dominant gene, although it cannot be ascertained if it is indeed Rpp4. The same behavior is exhibited by PI 200526 and PI 200487.

The segregation observed in PI 471904 indicates the presence of a dominant gene; however, this data was obtained after genotyping of the F2 plants by the progeny test. The previous assessment of the material in F2 showed a segregation of 113R for 93S, which matches the proportion of 1:1 ($\chi^2=2.142$ P=0.25-0.10). This fact occurred due to the presence, in this material, of a gene with incomplete dominance. The incomplete dominance led to an error in the phenotypic assessment of F2, resulting in that the heterozygotes were sometimes considered to be resistant and sometimes considered to be susceptible.

PI 200456 has an ASR-resistant recessive gene. The same fact was observed by the present invention for PI 224270, which also has a recessive gene for resistance. This is the first time a recessive gene conferring the phenotype of resistance to Asian Soybean Rust (ASR) has been reported. PI 230970, cited in the literature as the source of the Rpp2 dominant gene, shows distorted segregation results and the data do not match the 3:1 or 9:7 segregations ($\chi^2=4.272$ P<0.05).

Figure 1:
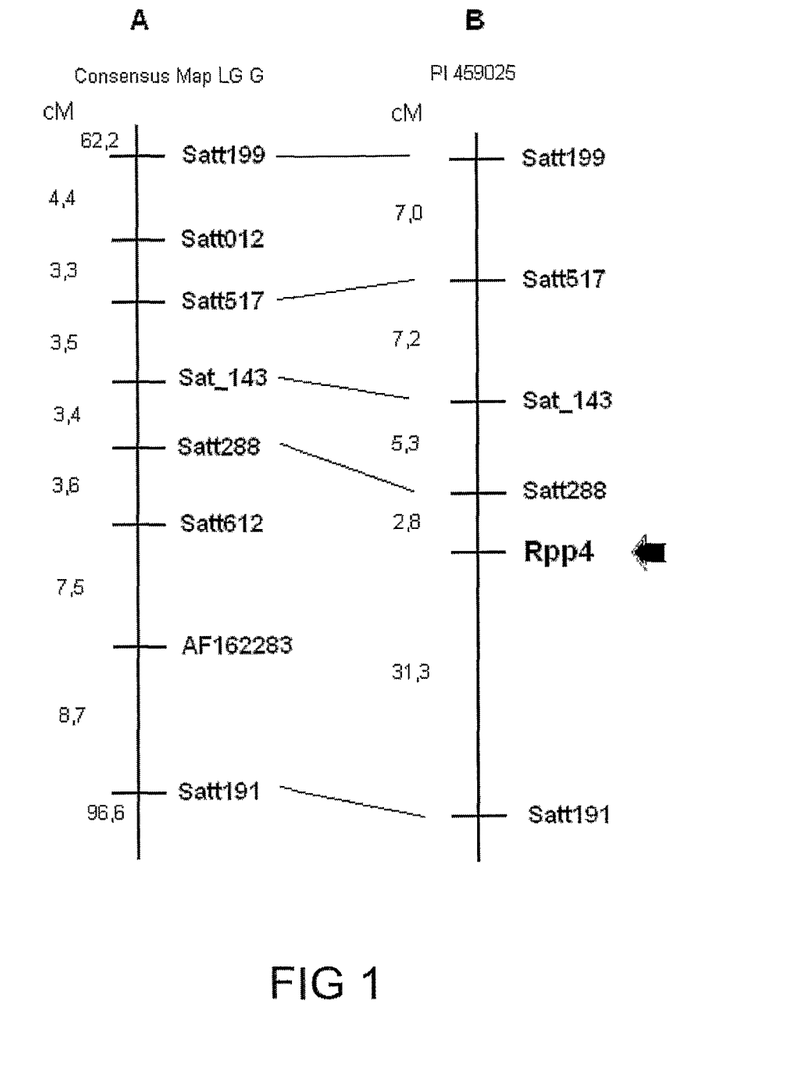
Figure 2:
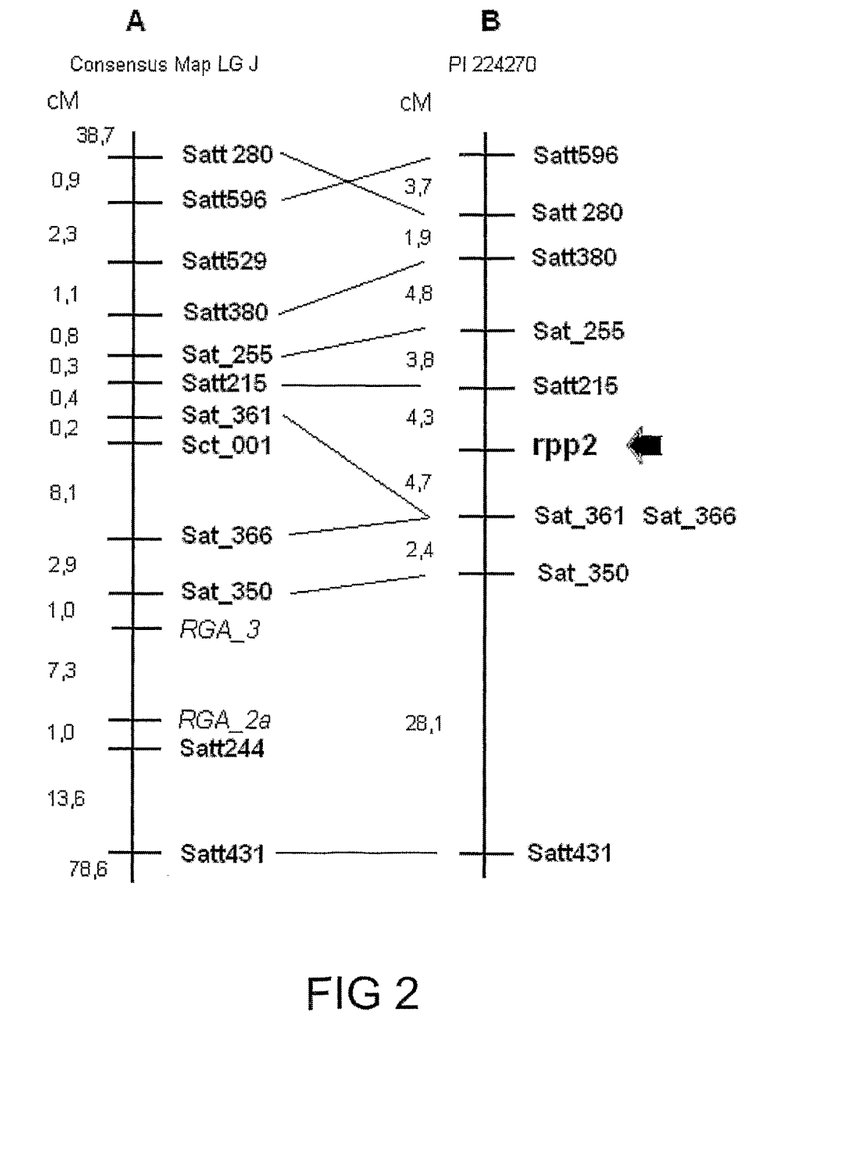

With regard to the genetic mapping data, after the genotyping of the individuals with the primers of the region in which the gene was identified, a linkage map of the populations was constructed. The resistance gene identified in the original source of Rpp4 (PI 459025) was mapped on linkage group G, at 2.8 cM of the Satt228 primer (FIG. 1). In the region below this gene, the closest primer was Satt191, at 31.3 cM. There are other primers in this region that may be closer; however, they could not be used in the mapping, since none of them was polymorphic for the crossing.

Figure 3:
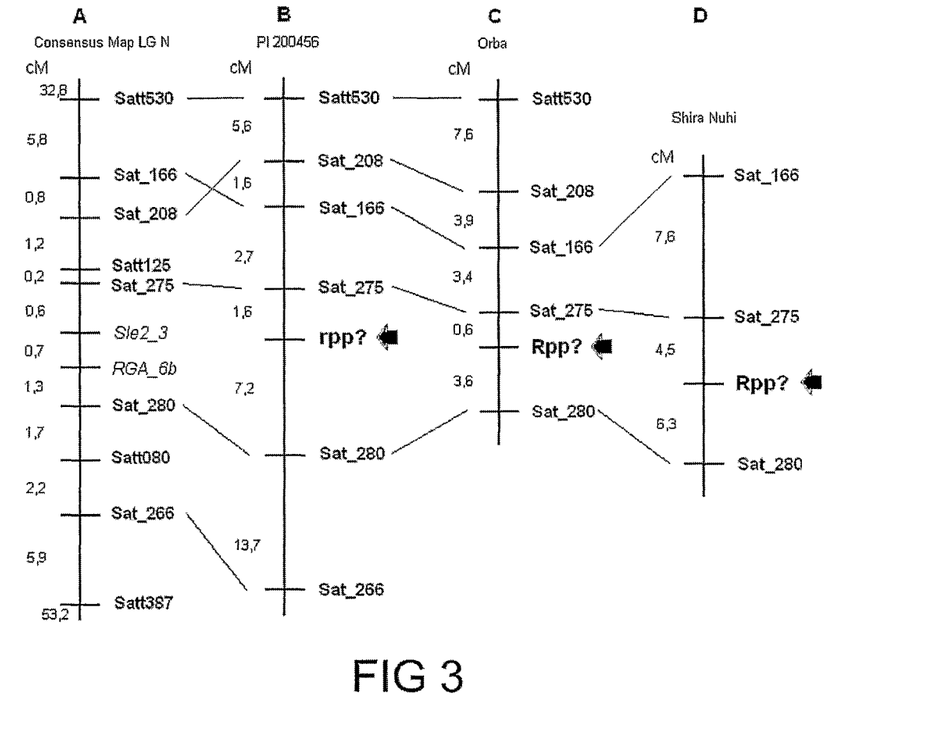
Figure 4:
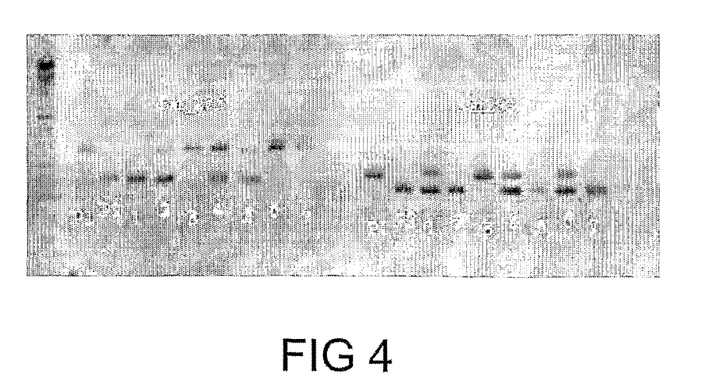
FIG. 4. Selection in F2 of individuals carrying 2 ASR-resistance genes. P1 represents PI 200456, source of Rpp5 and P2 represents PI 459025, source of Rpp4. Sat_275 is genetically linked to Rpp5; therefore, it is necessary to identify the individuals having the same pattern of bands as P1. Satt288 is linked to the resistance gene identified in the original source of Rpp4, so individuals with the amplification pattern of P2 are identified. In this case, only individual 7 will be selected as the carrier of the 2 resistance genes.

The recessive gene of PI 224270 was mapped on linkage group J, in a region which is rich in SSRs and other resistance genes, between primers Satt215 (4.3 cM) and Sat_361 (4.7 cM), as shown in FIG. 3. Since this region is rich in very close SSR markers, the use of a larger number of markers could better solve the distances, but only the markers listed in FIG. 3 could be used for crossing.

In linkage group N, recessive gene PI 200456, the gene with incomplete dominance of PI 471904 (Orba) and the dominant gene of PI 200526 (Shira Nuhi) were mapped at the same position, although the distances between the adjacent primers were different (FIG. 3). The gene of PI 200456 is at a distance of 1.6 cM from primer Sat_275 and of 7.2 cM from primer Sat_280, whereas in Orba these distances relative to the gene are of 0.6 cM and 3.6 cM and of 4.3 cM and 6.5 cM for the Shira Nuhi gene. Even with these data, it is still not possible to ascertain whether the alelles are from the same locus or from different loci. It is also not possible to test whether the genes from the N group are in the Rpp1 or Rpp3 locus. Therefore, the genes from these materials will be temporarily without a nomenclature designation, and will be referred to in the present invention as Rpp5 for PI 200487, PI 200526 and PI 472904 and as Rpp5 for PI 200456.

TABLE 1

Table 1. Rust-resistant parents crossed with susceptible parent CD 208 to enable segregation of the resistance genes. The plants obtained are derived from F2 families characterized by the $F_{2-3}$ progeny test. Chi-square tests were used to determine whether the results obtained were within the results expected.

| Resistant parent | $F_2$ Test | | | | | $F_{2-3}$ Test | | | | | |
|---|---|---|---|---|---|---|---|---|---|---|---|
| | # of Plants | | | Expected | | # of Plants | | | | Expected | |
| | R | S | Total | ratio | $X^2$ | R | H | S | Total | ratio | $X^2$ |
| PI 200526 (Shira Nuhi) | 156 | 47 | 203 | 3:1 | 0.369 NS | 48 | 85 | 44 | 177 | 1:2:1 | 0.458 NS |
| PI 200487 (Kinoshita) | 150 | 49 | 199 | 3:1 | 0.015 NS | 45 | 69 | 36 | 150 | 1:2:1 | 2.040 NS |
| PI 459025 (Bing nan) | 158 | 43 | 201 | 3:1 | 1.395 NS | 53 | 88 | 34 | 175 | 1:2:1 | 4.131 NS |
| PI 471904 (Orba) | 103 | 91 | 194 | 1:1 | 0.742 NS | 39 | 101 | 34 | 174 | 1:2:1 | 4.793 NS |
| PI 230970 | 123 | 64 | 187 | 3:1 | 8.487* | 19 | 108 | 73 | 200 | 1:2:1 | 30.44* |
| PI 200456 | 53 | 148 | 201 | 1:3 | 0.201 NS | 41 | 80 | 52 | 173 | 1:2:1 | 2.376 NS |
| PI 224270 | 43 | 152 | 195 | 1:3 | 0.904 NS | 34 | 87 | 53 | 174 | 1:2:1 | 4.149 NS |

*Statistical indicator of the significance level of the Chi-square value (p = 0.05).

TABLE 2

Table 2. For each crossing, the corresponding allele, the number of tested SSR loci, the percentage of polymorphic parents, the number of SSR used for the construction of the map, and the number of individuals genotyped in the mapping.

| Resistant Parent X Coodetec 208 | Rpp alelle | # of SSRs tested | % of Polymorphic SSRs | # of SSRs used in the mapping | # of individuals used in the mapping |
|---|---|---|---|---|---|
| PI 224270 | rpp2(?) | 177 | 38 | 10 | 174 |
| PI 230970 | Rpp2(?) | 175 | 36 | — | — |
| PI 459025 (Bing nam) | Rpp4(?) | 169 | 41 | 10 | 175 |
| PI 200456 | Rpp5 | 182 | 40 | 12 | 173 |
| PI 200526 (Shira Nuhi) | Rpp5 | 192 | 43 | 14 | 177 |
| PI 200467 (Kinoshita) | Rpp5 | 190 | 42 | — | — |
| PI 471904 (Orba) | Rpp5 | 177 | 40 | 13 | 174 |

Example 2

Gene Pyramiding Process

ASR-resistance is variety-specific, and therefore genotypes carrying only one resistance gene may have their effectiveness overcome within a short period of time. In order to obtain lasting and broad-spectrum resistance, the largest possible number of resistance genes should be gathered in a single material. Said gathering process is known as pyramiding and is facilitated with the aid of distinct molecular markers, genetically linked to the various resistance genes. The use of molecular markers enables the indirect monitoring of the introduction of different genes, which is an arduous and not very precise task when performed only by resistance phenotypic assessment.

In order to do so, it is necessary to select contrasting parents for resistance genes to the diseases of interest and to identify the varieties of the pathogen of greater importance for the region for which the new cultivars are intended, thus making gene pyramiding a useful process in genetic improvement programs. For these purposes, studies on the inheritance of resistance to the varieties selected from crossings between resistance sources and the susceptible cultivar of interest are made. Identifying molecular markers linked to the different resistance genes; obtaining isolines containing the resistance genes and the corresponding molecular markers, normally by backcrossing; validating the molecular markers which are able to specifically discriminate each of the resistance genes, so as to avoid problems with false positives; in addition to obtaining the isolines which are interbred for the purpose of pyramiding the resistance genes.

The Rpp5 genes, as well as the genes identified in the original sources of Rpp2 and Rpp4, which impart resistance to ASR, were positioned in the consensus linkage map, and therefore it is possible to select a set of markers genetically linked to each gene. In the present invention, the sources of Rpp5 (PI 200456), the recessive gene of PI224270 (probable rpp2), the dominant gene identified in the original source of Rpp4 (P1459025) and the susceptible cultivar Coodetec 205 were used in the pyramiding of the 3 ASR resistance genes.

SSR molecular makers in the proximity of the resistance genes, with a distance of 6 cM or less from the gene, were selected from the soybean consensus linkage map. Eleven markers were selected from linkage group N for gene Rpp5, eighteen markers from group J (probable rpp2), and seven markers from linkage group G were selected for the gene present in the source of Rpp4. The sequence of primers for each marker was obtained from the website www.sovbase.org.

Genomic DNA was extracted from the young and healthy leaves of the 4 genotypes, according to the Saghai-Maroof protocol with modifications. The SSR loci were amplified by PCR. The amplified fragments were separated in MetaPhor agarose gel at 3% and checked for polymorphism among the 4 genotypes. The 2 closest markers flanking each gene which showed polymorphic bands among all the genotypes were selected for subsequent analysis. By using two markers flanking the resistance genes, the selection efficiency is expected to be close to 100%.

Markers Sat_275 and Sat_280 were selected for Rpp5. Markers Sat_255 and Satt215 were selected for the recessive gene of PI 224270, and Sat288 and Satt612 were used for the gene present in the source of Rpp4. The fragments amplified by primers Sat_275 and Sat_280 in PI 200456 correspond to resistance gene Rpp5. The fragments amplified by primers Sat_255 and Satt215 in PI 224270 identify the resistance gene (probable rpp2) and the fragments amplified by primers Sat288 and Satt612 in PI 459025 select the resistance gene identified in the original source of Rpp4.

Based on these data, artificial crossings were conducted between the genotypes. PI 200456 (Rpp5) was hybridized with PI 224270 (probable rpp2). Fifteen F1 plants were obtained, which plants were used for hybridization with PI 459025 (original source of Rpp4). From this crossing 100 F1 plants were obtained.

Cotyledon DNA from each of the 100 F1 genotypes was extracted according to the Dellaporta method (1983) (Dellaporta, S. L.; Wood, J.; Hicks, J. B. 1983. A plant DNA minipreparation: Version II. Plant Molecular Biology. Report vol. 1: 19-21), with modifications, and the genotypes were analyzed with the markers of Rpp5, and of probable rpp2 and Rpp4. The heterozygote genotypes for said markers were selected and self-fertilized. The other materials were discarded.

In the F2 population resulting from this self-fertilization, the genotypes were segregating for the 3 genes. Three hundred F2 genotypes were obtained and individually identified, and cotyledon DNA was extracted according to the Dellaporta method (1983), with modifications.

A screening of the 300 individuals with the 3 SSR markers selected for each ASR resistance gene was carried out. The analysis with markers Sat_275 and Sat_280 identified the genotypes which exhibited the same amplified fragment pattern observed in PI 200456. For markers Sat_255 and Satt215, the genotypes which exhibited the same amplification pattern as PI 224270 were identified. The amplification pattern of markers Sat288 and Satt612 observed in PI 459025 was used as a parameter to identify the individuals when screening for these markers.

After said analyses, the data on the 3 pairs of markers were compared and the genotypes listed in the 3 cases were selected, since both had the 3 resistance genes. All the other genotypes were discarded.

The genotypes selected were then crossed with cultivar Coodetec 205. Six successive cycles of backcrossing and self-fertilization were performed. In each new cycle the analysis with the molecular markers was carried out, and only the genotypes having the 3 genes were selected and moved forward.

Continuing with said improvement program, some procedures should become routine, such as the continuous characterization of the genetic variability of the pathogens and of the host, the introduction of new sources of resistance and the identification of molecular markers linked to resistance alleles.

Example 3

Positional Cloning

Markers linked to each of the QTLs for resistance or tolerance to Asian soybean rust may be used in the positional cloning of the genes. The first step of this process consists of creating a physical map of a contig (contiguous overlapping of cloned DNA inserts) in the genomic region comprising one or more markers of the loci and of the gene of interest. The gene of interest is then identified and isolated in one or more clones present in the contig. Thus, the clone of a gene is obtained, to be used genetic studies, transformation and development of new phenotypes.

Markers mapped for resistance, especially those which are genetically and physically linked to the QTL or genes of interest are used in the identification of clones from genomic libraries, including, for example, soybean genomic libraries made in bacterial artificial chromosomes (BAC), yeast artificial chromosomes (YAC) or bacteriophage-derived artificial chromosomes. These are the preferred vectors for positional cloning, since they are able to carry a long DNA fragment.

Additionally, positional cloning is considered to be an efficient method for isolating a gene when its mechanism of action and product(s) are still unknown. There are some initial requirements for the cloning method, the first of which is the presence of individuals of a population with different genetic bases conditioning the trait of interest. The second requirement is that the genes which are responsible for the difference in the phenotype can be mapped to be positioned in locations in the genome.

The genetic mapping of the ASR resistance genes is the first step towards positional cloning, especially of the Rpp5 gene, located in linkage group N. The mapping of Rpp5 is relevant, since both recessive and dominant resistance alleles were detected at this locus. Since the alleles have different behaviors but confer the same phenotype, the cloning of the gene and the study of its products contributes to the understanding of the mechanism of action of the resistance genes.

Marek and Schoemaker (1997) (Marek F L, Schoemaker R C (1997) BAC contig development by fingerprint analysis in soybean. Genome 40: 420-427), constructed a BAC (bacterial artificial chromosome) genomic library for soybeans, with an average insert size of 150 k, suitable for use in physical mapping and positional cloning. The soybean physical map, available at the website www.sovbase.org, although it is still being checked, has several constructed contigs. Additionally, the physical map was aligned with the genetic map, anchoring the BAC contigs to molecular markers. By adding the information from the physical map to the data from the genetic mapping of the Rpp5 gene, the cloning of genes which impart resistance to ASR becomes a reality.

The Rpp5 gene was genetically mapped in linkage group N, flanked by the markers of SSR Sat_275 and Sat_280. Contig WmContig404 from the soybean physical map encompasses this region of linkage group N and is formed by the alignment of 219 clones. Since this contig is too large, the 219 clones must be screened by PCR with the primers of Sat_275 and Sat_280. The purpose of said analysis is to find the clones having said markers and thus create a smaller contig, thereby eliminating the clones which are not in the interval between the two markers. Contigs WmContig404, WmContig562, WmContig5258 or WmContig6713, or any contig having a marker closer than 5 cM from the gene may be cited as non-limiting examples.

In the next step, the fragments forming the new contig are sequenced by shotgun sequencing to find new SSR markers in the region of the resistance gene. The sequencing also enables the construction of primers for SCAR markers to be developed or for the amplified product, after a PCR reaction, to be eluted from the gel and digested with a restriction enzyme cocktail, thereby generating molecular markers of the CAPs type.

The new markers obtained are used in the high-resolution genetic mapping, with a population of approximately 1,500 individuals (3,000 meiotic events), using the pooled-sample mapping strategy proposed by Churchill et al. (1993) (Churchill G A, Giovannoni J J, Tanksley S D (1993) Pooled-sampling makes high-resolution mapping practical with DNA markers. Proc. Natl. Acad. Sci. 90: 16-20). By analyzing 3,000 meiotic events, there is a 95% probability of identifying a recombination within less than 0.1 cM. Considering the size of the inserts in the BAC library, if one marker is mapped at 0.1 cM or less from the gene, there is a great chance that both will be located in the same clone.

The closest marker to the gene is then used to isolate a single BAC clone from among the ones previously selected as shown by Tanksley et al. (1995) (Tanksley S D, Ganal M W, Martin G B (1995) Chromosome landing: a paradigm for map-bases gene cloning in plants with large genomes. Trends in Genetics 11: 63-68). A radioactive probe is constructed from the soybean DNA fragment from the isolated clone using the random primer technique. This probe is used in the hybridization in a cDNA library built from leaf tissue from a resistant genotype challenged with the ASR fungus.

After hybridization, few resistance gene candidates are identified. The sequences of the candidate products are determined, databases such as BLAST are used, and said sequences are compared with other sequences already deposited, in an attempt to find homology with resistance genes already known.

The confirmation of which cDNA sequence corresponds to the target gene is obtained after: (1) establishing the relationship between the sequence and other known resistance genes; (2) demonstrating the cosegregation of the candidate sequence with the resistance phenotype; (3) analyzing the gene expression of susceptible and resistant genotypes inoculated with the fungus using the Northern Blot technique, (4) transforming susceptible plants with the candidate sequence for complementation of the phenotype.

Example 4

Development of Resistant Cultivars

Another application of the present invention is in the creation of new ASR-resistant soybean cultivars from exotic resistance sources, such as the introductions of plants of the present invention. In this case, the new cultivar may be obtained by hybridizing an exotic PI, carrying one or more ASR-resistance genes and/or alleles described in the present invention, with a line or cultivar which is susceptible to ASR but agronomically adapted to the country or region for which the new cultivar is to be obtained. After obtaining this $F_1$ seed, the generation advancement is carried out using different classic improvement methods, such as, Bulk, SSD, MSSD, Backcrossing, among others and not limited thereto, as described in the "Background of the Invention" section, according to the breeder's preference. The resistant plants may be selected throughout the generation advancement process by artificial inoculation of the spores of the fungus, or even by natural infection, or using selection assisted by the molecular markers described in the present invention (Examples 1 and 2).

As an example, PI 635026, which is resistant to ASR, was hybridined with adapted line TMGLM-3219, which is susceptible to ASR. The resulting $F_1$ seed was planted in a greenhouse to obtain $F_2$ seeds, which were also planted in a greenhouse and inoculated with an aqueous solution containing $50 \times 10^3$ P. pachyrhizi spores per ml. The resistance plants were selected and kept for the production of $F_3$ seeds. $F_{2:3}$ progenies were sown in a greenhouse and assessed for ASR-resistance, as before. The best resistance plants were individually gathered and the progenies ($F_{3:4}$) of these plants were sown in the field in the summer of 2004/2005. Individual plants were selected from among these progenies based on their agronomic appearance, originating $F_{4:5}$ progenies, which were sown in a greenhouse and once again assessed for ASR-resistance. Resistant plants were individually gathered, generating $F_{5:6}$ progenies which were sown in the field. A new selection of individual plants was made based on the agronomic appearance of the progenies, thus generating $F_{6:7}$ progenies which were designated CB06-953, CB06-954, CB06-955, CB06-956, CB06-957, CB06-958, CB06-959, CB06-960, CB06-961, CB06-962, CB06-963, CB06-964, among other progenies. Seeds from these progenies were multiplied in the winter and in the summer of 2006/2007 and were included in VCU (Value of Culture and Use) assays.

The assays were carried out by random triplet repeat block delineation, and the experimental portion was formed by four 5-meter-long lines spaced by 45 cm. The assays were performed in three different environments (Cambé, Campo Mourão and Ponta Grossa) in the state of Paraná (Brazil). In Cambé, two assays were performed, one of which had full disease control, with 3 fungicide applications (triazoles and strobilurins), while the other did not receive any fungicide application. Among the traits assessed are grain yield and progression of disease severity, which is assessed according to the methodology described by Godoy, et al. (2006) (GODOY, C. V., KOGA, L. J. & CANTERI, M. G. (2006) Diagrammatic scale for assessment of soybean rust severity. Fitopatologia Brasileira 31:063-068).

Figure 5:
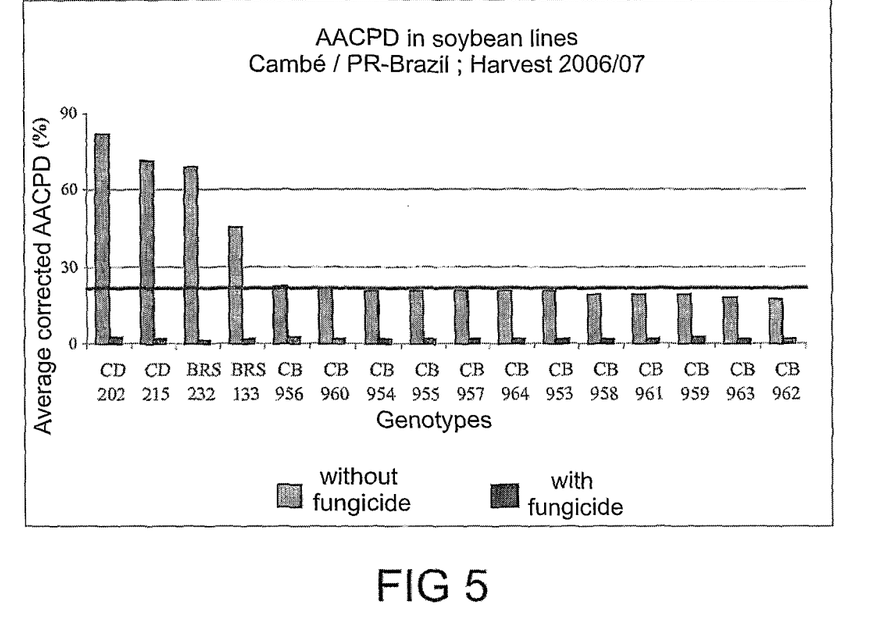
FIG. 5. Disease severity—shows the progression of the disease in cultivars susceptible to ASR (CD 202, CD 215, BRS 232, BRS 133) compared to resistant lines (CB06-953, CB06-954, CB06-955, CB06-956, CB06-957, CB06-958, CB06-959, CB06-960, CB06-961, CB06-962, CB06-963, CB06-964, among others). Clearly, the resistant lines presented an average reduction of approximately 60% in disease severity without the use of fungicides, compared to the ASR susceptible lines.
Figure 6:
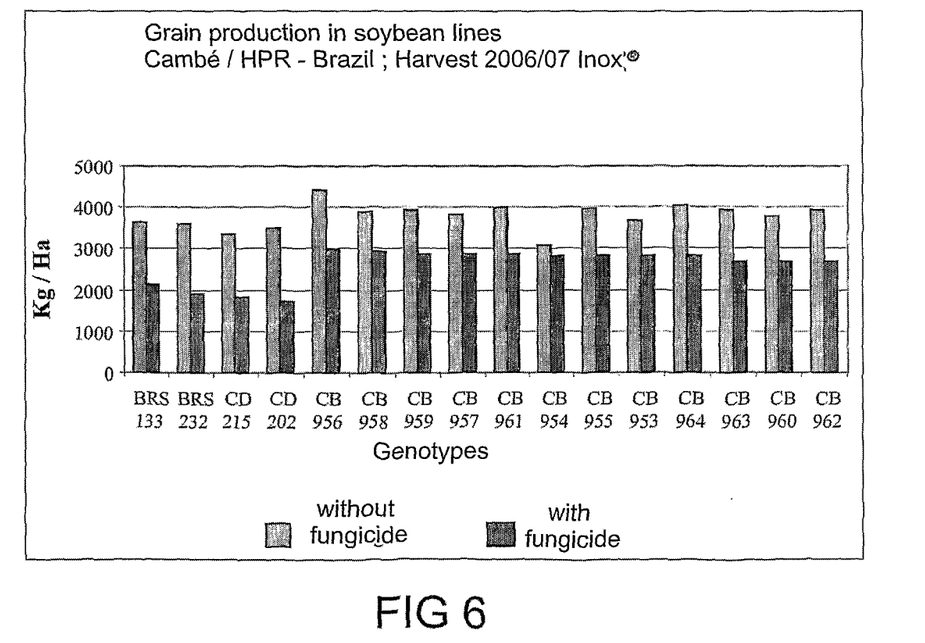
FIG. 6. Grain yield (Kg/Ha) in soybean lines resistant to Asian rust. Twelve sister lines derived from the cross between PI 635026 X TM-GLM-3219 were assessed under field conditions with a high rust infestation. The graph shows the yield (Kg/Ha) in two different conditions (with and without fungicide) for each one of the lines. The susceptible cultivars CD 202, CD 215, BRS 232 and BRS 1333 were used as susceptibility patterns.

FIG. 5 shows the progression of the disease in ASR-susceptible cultivars (CD 202, CD 215, BRS 232, BRS 133) compared to the resistant lines, such as, for example, CB06-956, CB06-960, CB06-954, CB06-955, CB06-957, CB06-964, CB06-953, CB06-958, CB06-961, CB06-959, CB06-963, CB06-962, among other lines. Clearly, the resistant lines showed, in the absence of fungicides, an average reduction of approximately 60% in the severity of the disease when compared to the ASR-susceptible lines. FIG. 6 shows that this reduction in severity drastically reflected on grain yield and, in the absence of fungicides, all lines showed higher yield than all susceptible patterns.

Example 5

Genetic Control Associated with the Use of Fungicides

The use of fungicides is proving to be an alternative method in ASR control. In this context, another application of the present invention becomes evident. The association of genetic control—by means of the ASR-resistance/tolerance genes/alleles previously described, or even through other genes/alleles of similar effect—with chemical control through use of fungicides is proving to be a new method of ASR control. In this case, the producer would have more certainty about the control, and the durability of other rust-resistance/tolerance genes could be extended.

Nowadays, ASR is controlled by using fungicides from the groups of the triazoles, strobilurins, benzimidazoles, prothioconazole, protilcnazole and others. But for the disease to be effectively controlled, the moment of application is critical. After the detection of the disease in the plants, a two-day delay in the application may, under favorable conditions, make total damage control impossible. Research results have shown that missing the fungicide "application timing" produces 60% damage, even when the number of sequential applications is increased. In these conditions, the residual effect of the fungicide is considerably reduced. Therefore, a new method of ASR control, associating the use of genetically resistant cultivars with the application of fungicides is required.

Another aspect to be considered relates to the efficacy of the different types and brands of fungicides recommended for ASR control, since they exhibit significant variations. Additionally, some fungicides are only recommended in the so-called preventive applications, that is, when applied before the symptoms of the disease (lesions) appear (Godoy, C. V. & Canteri, M. G. "Efeitos protetor, curativo e erradicante de fungicida no controle de ferrugem da soja causada por *Phakopsora pachyrhizi*, em casa de vegetação". Fitopatologia Brasileira, v. 29 n. 1, 97-101, January-February, 2004; Soares, R. F., Rubin, S. A. L.; Wielewicki, J. G. O. "Fungicida no controle da ferrugem asiática (*Phakopsora pachyrhizi*) e produtividade da soja". Ciência Rural, v. 34, n. 4, p 1245-1247, July-August, 2004). In practice, however, this is not always possible, since in addition to climatic and operational conditions which may prevent the application, the producer is always trying to delay the application in order to reduce the number of applications during the culture cycle. Thus, most applications are curative rather then preventive.

Therefore, the best time and the number of applications of the fungicide for the effective control of the disease become different in materials carrying ASR-resistance or -tolerance genes. Moreover, the chemical molecules which did not provide an efficient control of the disease may start providing an efficient control as the resistance lesion (RB lesion) produces less sporulation.

An experiment was conducted under field conditions in 2006/07, in Cambé, PR, to determine the ideal fungicide application timing for a resistant line carrying an ASR-resistance gene. Soybean cultivar BRS 133, which has a similar cycle but is completely susceptible to ASR, was used as a basis of comparison. The fungicide chosen for the chemical control of ASR was the commercial product Opera® (BASF), a commercial mixture of strobilurin (pyraclostrobin) and triazole (epoxiconazole). However, any commercially available fungicide may be used. The assay was conducted in random triplet repeat blocks, and the chemical treatments for BRS 133 and for the resistant line were:

Blank: without the application of the fungicide Opera® (Blank) but with the application of the fungicide Derosal® only for controlling late-cycle diseases;

Control: three applications (reproductive stages R2, R4, and R5.5) of Opera®

6 treatments with single applications of the fungicide Opera® in different development stages (R2; R3; R4; R5.1; R5.3; R5.4)

The summary of the treatments is exemplified in Table 3.

TABLE 3

| Treatment | # of applications | Stage of Application |
|---|---|---|
| T1 (Blank) | 0 | — |
| T2 (Control) | 3 | R2, R4, R5.4 |
| T3 | 2 | R2, R5.1 |
| T4 | 1 | R2 |
| T5 | 1 | R3 |
| T6 | 1 | R4 |
| T7 | 1 | R5.1 |
| T8 | 1 | R5.3 |
| T9 | 1 | R5.4 |

The severity was quantified every fifteen days with the aid of the diagrammatic scale developed by Godoy et al. (2006) (Godoy, C. V; Koga, L. J. & Canteri, M. G. Diagrammatic scale for assessment of soybean rust severity. Fitopatologia Brasileira. Fitopatologia Brasileira, v. 31, p. 63-68, 2006). The data was subject to variance analysis by the F test and the differences between the averages, when significant, were compared using Tukey's test (5%), SASM-Agri software (Canteri et al., 2001). Canteri, M. G., Althaus, R. A., Virgens Filho, J. S., Giglioti, E. A., Godoy, C. V. Sasm—Agri: Sistema para análise e separação de médias em experimentos agrícolas pelos métodos Scott—Knott, Tukey e Duncan. Revista Brasileira de Agrocomputação, v. 1, n. 2, p. 18-24. 2001).

Figure 7:
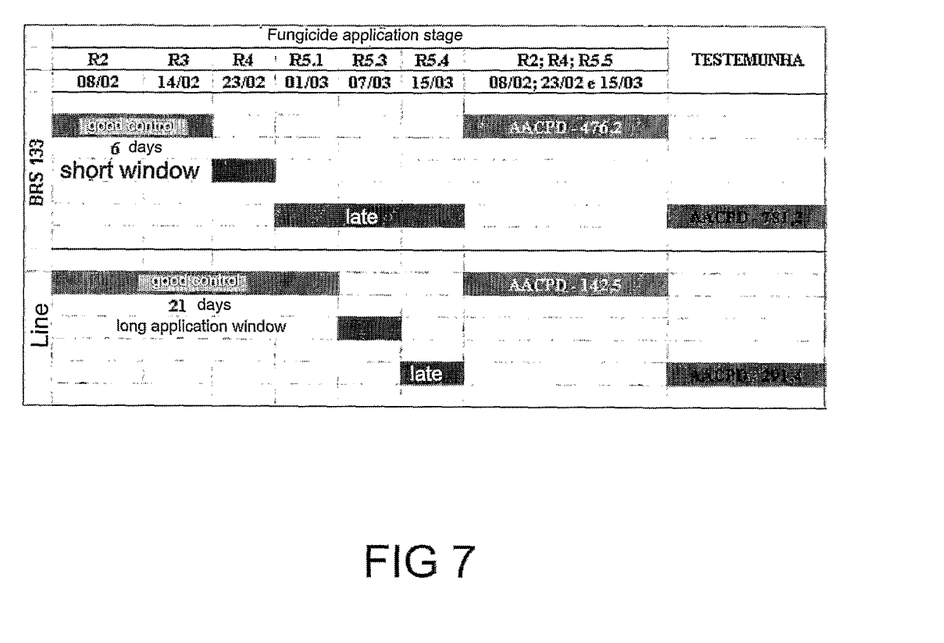
FIG. 7. Fungicide application window.

FIG. 7 summarizes the result of the use of fungicide in materials with resistance/tolerance to ASR, whose data show a delay in the beginning of the development of the disease and significant reduction of its process in the resistance line. It has been observed that when the resistant line received only one fungicide application in stage R5.1, the average AUDPC (Area Under the Disease-Progress Curve) was similar to that of the Control (resistant line with 3 fungicide applications) and did not significantly differ therefrom. Cultivar BRS 133, on the other hand, had to receive a fungicide application in stage R3 to exhibit an AUDPC similar to that of its Control (BRS 133 with 3 fungicide applications) and not to differ significantly therefrom. This shows that the ASR control in the resistant line is effective with only one fungicide application at any moment between reproductive stages R2 and R5.1. For BRS 133, on the other hand, the control is effective only between stages R2 and R3.

In the resistant line, with the application of fungicide in stage R5.4, the AUDPC significantly differs from that observed in the control treatment, the severity is high and the disease control at this point is ineffective. For BRS 133 this situation is observed as early as in stage R5.1. In the other stages of control, there is a medium level of control.

This result shows that the presence of the resistance gene delays the development of rust, thus enabling a reduction in the number of applications and a larger application window for the spraying of the fungicide. Consequently, the use of fungicides associated with the use of cultivars with genetic resistance enables the control of Asian soybean rust to be made in a more effective manner and at lower costs (FIG. 7).

The present invention has been described based on examples of embodiments; it is understood, however, that it encompasses other embodiments and is limited only by the scope of the appended claims.

The invention claimed is:

1. A method for identifying and selecting soybean *Glycine max* individuals carrying a phenotypic trait related to resistance and/or tolerance to Asian soybean rust *Phakopsora pachyrizi* comprising:

a) extracting nucleic acid from a plant of any soybean genotype;
b) assaying the extracted nucleic acid for at least one molecular marker mapped at 10 cM or less from the Rpp5 locus to obtain an amplification pattern of the at least one molecular marker;
c) comparing the amplification pattern obtained in step (b) with an amplification pattern of the Asian soybean rust resistant genotypes PI 200456, PI 200526, PI 200487 or PI 471904, wherein the amplification pattern of the Asian soybean rust resistant genotypes PI 200456, PI 200526, PI 200487 or PI 471904 was obtained using the same at least one molecular marker as that used in step b); and
d) selecting plants that exhibit the same amplification pattern as any one of the Asian soybean rust resistant genotypes PI 200456, PI 200526, PI 200487 or PI 471904;
wherein said Rpp5 locus is mapped in linkage group N, flanked by markers Sat 275 and Sat 280.

2. The method according to claim 1, characterized in that said molecular marker(s) is selected from the group consisting of RFLPs, RAPDs, AFLPs, SSRs, SNPs, ESTs and RGA probes.

3. The method according to claim 1, characterized in that said molecular marker(s) is selected from the group consisting of A426_2, Sle_003, i4_2, Sat_084, Satt393, Satt584, Satt485, Sat_166, Sat_208, BLT049_1, Bng095_2, OP_F13, Satt125, Sat_275, Sle_3, RGA_6b, OP_U09b, mO128_1, Sat_280, Satt080, and Sat_266.

4. The method according to claim 1, characterized in that the nucleic acid is extracted from any plant tissue of said soybean *Glycine max* individuals.

5. The method according to claim 1, characterized in that the molecular marker is detected by PCR or a sequencing technique.

* * * * *